US012103688B2

United States Patent
Sun

(10) Patent No.: US 12,103,688 B2
(45) Date of Patent: Oct. 1, 2024

(54) HIGH-TEMPERATURE STERILIZATION AIR CONDITIONING SYSTEM FOR AIRPLANE AND STERILIZATION METHOD

(71) Applicant: NANJING UNIVERSITY OF AERONAUTICS AND ASTRONAUTICS, Nanjing (CN)

(72) Inventor: Jianhong Sun, Nanjing (CN)

(73) Assignee: NANJING UNIVERSITY OF AERONAUTICS AND ASTRONAUTICS

( * ) Notice: Subject to any disclaimer, the term of this patent is extended or adjusted under 35 U.S.C. 154(b) by 664 days.

(21) Appl. No.: 17/233,440

(22) Filed: Apr. 17, 2021

(65) Prior Publication Data

US 2021/0269164 A1  Sep. 2, 2021

Related U.S. Application Data

(63) Continuation of application No. PCT/CN2020/095745, filed on Jun. 12, 2020.

(30) Foreign Application Priority Data

Feb. 28, 2020  (CN) .......................... 202010129659.2

(51) Int. Cl.
  *B64D 13/08* (2006.01)
  *A61L 9/16* (2006.01)
  *B64D 13/06* (2006.01)
(52) U.S. Cl.
  CPC ................ *B64D 13/08* (2013.01); *A61L 9/16* (2013.01); *A61L 2209/16* (2013.01); *B64D 2013/0618* (2013.01); *B64D 2013/0688* (2013.01)

(58) Field of Classification Search
  CPC ............ B64D 13/08; B64D 2013/0618; B64D 2013/0688; B64D 2013/0651;
  (Continued)

(56) References Cited

U.S. PATENT DOCUMENTS 4,308,993 A * 1/1982 Buss ...................... B64D 13/08
                                                     60/648
5,343,692 A * 9/1994 Thomson ............... B64D 13/06
                                                     60/785
(Continued)

FOREIGN PATENT DOCUMENTS

CN  101590798  12/2009
CN  203957790  11/2014
CN  105620761  6/2016

*Primary Examiner* — Regina M Yoo
(74) *Attorney, Agent, or Firm* — Treasure IP group, LLC

(57) ABSTRACT

An aircraft Ultra-High-Temperature Sterilization Air Conditioning System (UHTS-ACS) and a sterilization method are provided. An ultra-high-temperature sterilization recirculated air device is added on the basis of a traditional aircraft air conditioning system. The recirculated air device includes an ultra-high-temperature sterilization recirculated airline (9), a heater (26), a high-temperature injection mixing chamber (27) and a primary heat exchanger (12) bypass. The recirculated airline is connected to the high-temperature injection mixing chamber (27). After being mixed with high-temperature engine bleed air (I) under the injection action of an injector (28), the mixed high-temperature gas enters a compressor (15) through the primary heat exchanger (12) bypass to be compressed and heated, is regulated to a suitable temperature through cooling of a secondary heat exchanger (13) and a turbine (16), and then is supplied to an aircraft cabin. The system and method can perform ultra-high-temperature sterilization on the recirculated air of the aircraft air conditioning system, thus ensuring the cleanliness of the aircraft cabin supply air and the hygiene safety (Continued)

of people on board, and thereby achieving the effects of killing the infectious viruses and inhibiting cross infection among people.

6 Claims, 2 Drawing Sheets

(58) Field of Classification Search
CPC ... B64D 13/06; B64D 2013/0603; A61L 9/16; A61L 2209/16; Y02T 50/50
See application file for complete search history.

(56) References Cited

U.S. PATENT DOCUMENTS

| | | | |
|---|---|---|---|
| 2015/0121909 A1* | 5/2015 | Koenig | B64D 13/06 |
| | | | 62/61 |
| 2016/0311540 A1* | 10/2016 | DeValve | B64D 13/08 |
| 2016/0355271 A1* | 12/2016 | Bruno | B64D 13/08 |
| 2018/0305030 A1* | 10/2018 | Galzin | B64D 13/06 |
| 2018/0370636 A1* | 12/2018 | Laborde | B64D 13/04 |
| 2019/0009912 A1 | 1/2019 | Matsui | |
| 2021/0197975 A1* | 7/2021 | Zhu | B01D 53/0438 |

* cited by examiner

HIGH-TEMPERATURE STERILIZATION AIR CONDITIONING SYSTEM FOR AIRPLANE AND STERILIZATION METHOD

CROSS REFERENCE TO RELATED APPLICATION

This application claims priority to a PCT application PCT/CN2020/095745, filed on Jun. 12, 2020, which in turn takes priority of Chinese Application No. 202010129659.2, filed on. Feb. 28, 2020. Both the PCT application and Chinese Application are incorporated herein by reference in their entireties.

TECHNICAL FIELD

The present invention relates to the fields of aircraft and civil aviation, and in particular to an aircraft airborne air conditioning system.

BACKGROUND ART

With the development of civil aviation, aircraft are increasingly chosen as a means of transportation for ordinary travel. In recent years, the number of flights and trips of civil aircraft has increased significantly. During the flight, the aircraft cabin is a closed space environment, and the health, safety and comfort of the people in the cabin are key concerns. An aircraft air conditioning system is an important mechanism system to provide a healthy and comfortable environment for aircraft passengers and crew by regulating the pressure, temperature, humidity and other parameters of the aircraft cabin environment.

A series of influenza viruses and coronaviruses have been rampant in recent years, such as the SARS virus in 2003, the HINI virus in 2009, and then the Ebola virus and 2019-nCov, etc. Related reports indicate that transmission in the means of transportation is also one of the ways in which the virus spreads. The high infectiousness and case fatality rates of these viruses have led to rejection and fear to public transportation during the epidemic. During the novel coronavirus epidemic in 2020, public transportation was almost paralyzed, including the civil air transportation system, which was severely affected. For civil aircraft, an aircraft cabin is a closed small space. From the economy, engine performance and other considerations, the aircraft air conditioning system contains part of circulated air in the cabin, so the air quality in the cabin involves safety and health of the passengers, and how to protect the public health security in the aircraft cabin during the epidemic is also one of the key concerns for the aircraft air conditioning system.

Currently, the airborne air conditioning system mainly used in civil airliners is a 50/50 mixed air ratio air supply system. In this air supply system, 50% of the mixed gas comes from the fresh air outside the cabin (usually the engine bleed air), and the other 50% is the recirculated air in the cabin. This part of recirculated air may contain viruses, bacteria and other harmful components exhaled by the carrier. The air conditioning system has complete filtering and cleaning components, but they are for the known viruses and bacteria. For novel viruses, especially unknown and highly infectious viruses, it is not a complete solution. During epidemics of some novel infectious viruses or bacteria, this is a great threat to the health and life safety of passengers. Therefore, there is an urgent need for a novel aircraft air conditioning system that can kill infectious viruses and bacteria to ensure the health and safety of people in the aircraft cabins, provide safe and reliable rapid transportation capacity for the prevention of large-scale infectious diseases and the national economy transportation guarantee during the epidemic, and ensure the normal operation of the national economy.

In the present invention, by using the aircraft engine bleed air and compressor-turbine mechanism, ultra-high-temperature sterilization are performed on the infectious viruses and bacteria in the recirculated air of the aircraft cabin under certain high temperature conditions by means of front-end mixing, thereby enhancing the air quality of the aircraft cabin supply air, inhibiting the transmissibility of aircraft cabin viruses, and ensuring the health and safety of aircraft passengers and crew on board.

SUMMARY OF THE INVENTION

An objective of the present invention is to solve the problem that the traditional aircraft air conditioning system cannot kill 100% of viruses and bacteria (especially some novel highly infectious viruses and bacteria) in the recirculated air, resulting in that the air quality of the aircraft cabin supply air cannot meet the requirement of non-infectiousness and solve the doubts of the passengers, and provide a novel aircraft air conditioning system, so that the recirculated air of the aircraft air conditioning system is subjected to ultra-high-temperature sterilization, thus ensuring the cleanliness of the aircraft cabin supply air and the hygiene safety of people on board (passengers and crew), and thereby achieving the effects of killing the infectious viruses (such as SARS, 2019-nCoV and the like) and inhibiting cross infection among people.

In order to achieve the above objective, the present invention is realized by an aircraft Ultra-High-Temperature Sterilization Air Conditioning System (UHTS-ACS) with the following features. The specific technical solution is as follows:

According to the system of the present invention, an ultra-high-temperature sterilization recirculated airline is added on the basis of a traditional aircraft air conditioning system. The system of the present invention mainly includes an ultra-high-temperature sterilization recirculated airline valve, a heater, a ultra-high-temperature injection mixing chamber, an injector, a primary heat exchanger bypass valve and components of the traditional aircraft air conditioning system.

The recirculated air passes through a recirculated air main line and enters an ultra-high-temperature sterilization recirculated airline and an ordinary recirculated airline, and the ultra-high-temperature sterilization recirculated airline is connected to an engine bleed air main line.

The ultra-high-temperature sterilization recirculated airline is provided with a one-way valve for controlling opening and closing of the branch and the heater.

The recirculated air is mixed with the engine bleed air in the ultra-high-temperature injection mixing chamber, and the ultra-high-temperature injection mixing chamber is provided with an injection device (injector).

The ordinary recirculated airline is provided with a one-way valve for controlling opening and closing of the branch.

There is a bypass in front of a primary heat exchanger, and the bypass is provided with a valve capable of controlling an air flow to bypass the primary heat exchanger.

Under normal working conditions, the ordinary recirculated airline valve is opened. The ultra-high-temperature sterilization recirculated airline valve is closed, and the primary heat exchanger bypass valve is closed. At this time, the ultra-high-temperature sterilization recirculated airline does not work, the recirculated air is mixed with cooled engine bleed air fresh air in the mixing chamber through the ordinary recirculated airline, and the mixed gas is supplied to a cabin.

Under special working conditions (for example, during epidemics of some novel infectious viruses or bacteria), the ordinary recirculated airline valve is closed, the ultra-high-temperature sterilization recirculated airline valve is opened, and the primary heat exchanger bypass valve is opened. At this time, the ultra-high-temperature sterilization recirculated airline works, the ordinary recirculated airline does not work, and the recirculated air is heated by the heater and then mixed with the high-temperature engine bleed air in the high-temperature injection mixing chamber under the injection action of the injector in the mixing chamber, so that the mixed gas has higher temperature, thereby achieving the effect of sterilization. The mixed gas enters the compressor through the primary heat exchanger bypass to be compressed by the compressor such that the temperature of the mixed gas further increases, thereby further performing sterilization. Finally, the mixed gas is regulated to a suitable temperature through the heat dissipation of the secondary heat exchanger and the cooling of the turbine, and then is supplied to the cabin. The injector can make the recirculated air thoroughly mixed with the engine bleed air in the high-temperature injection mixing chamber through the injection action. Therefore, the temperature of the mixed gas is more uniform such that a better sterilization effect is achieved, and the power compensation can be reduced such that the cost can be saved.

Based on the above aircraft Ultra-High-Temperature Sterilization Air Conditioning System (UHTS-ACS), the specific operation and implementation method of the system of the present invention is as follows:

1. Under special working conditions (for example, during epidemics of some novel infectious viruses or bacteria), the ordinary recirculated airline valve is closed, and the ultra-high-temperature sterilization recirculated airline valve is opened. The ultra-high-temperature sterilization recirculated airline works, the ordinary recirculated airline does not work, and the recirculated air enters the ultra-high-temperature sterilization recirculated air line through the ultra-high-temperature sterilization recirculated airline valve.

2. The recirculated air enters the ultra-high-temperature sterilization recirculated airline and then is heated by the heater, so that the temperature increases and preliminary sterilization is performed on harmful bacteria and viruses in the gas.

3. The recirculated air in the ultra-high-temperature sterilization recirculated airline rapidly enters the high-temperature injection mixing chamber under the injection action of the injector, and is thoroughly mixed with the high-temperature engine bleed air (usually up to 400 K or above), so that the mixed gas has higher temperature, thereby further achieving the effect of sterilization. Due to the action of the injector, the gas is mixed more thoroughly in the high-temperature mixing chamber, and the temperature is more uniform, thereby further enhancing the sterilization effect.

4. At this time, the primary heat exchanger bypass valve is opened, and the mixed gas passes through the primary heat exchanger bypass to avoid heat exchange and cooling of the primary heat exchanger, so that the continuous ultra-high-temperature sterilization of the mixed gas can be ensured.

5. Then the mixed gas enters the compressor to be compressed by the compressor such that the temperature of the mixed gas further increases, thereby further performing sterilization.

6. Finally, the mixed gas is regulated to a suitable temperature through the heat dissipation of the secondary heat exchanger and the cooling of the turbine, and then is supplied to the cabin.

Preferably, the heater may be omitted in the system. Thereby lowering the mass of the aircraft air conditioning system, reducing the aircraft compensation loss and saving the cost.

Compared with the existing system and technology, the above technical solution adopted by the present invention has the following technical effects:

According to the aircraft UHTS-ACS of the present invention, by adding the ultra-high-temperature sterilization recirculated airline, while the aircraft air conditioning system meets certain economy, the recirculated air of the aircraft air conditioning system is subjected to ultra-high-temperature sterilization, thereby greatly reducing harmful components in the air, enhancing the air quality of the aircraft cabin supply air, and preventing the infectious viruses and bacteria from returning to the cabin through the recirculated air system and causing cross infection. Thereby, the transmissibility of aircraft cabin viruses is inhibited, the health and safety of aircraft passengers and crew on board are enhanced, and safety and reliability of civil air transportation under highly infectious epidemic conditions are ensured.

BRIEF DESCRIPTION OF THE DRAWINGS

The present invention will be further described below in conjunction with the accompanying drawings.

Figure 1:
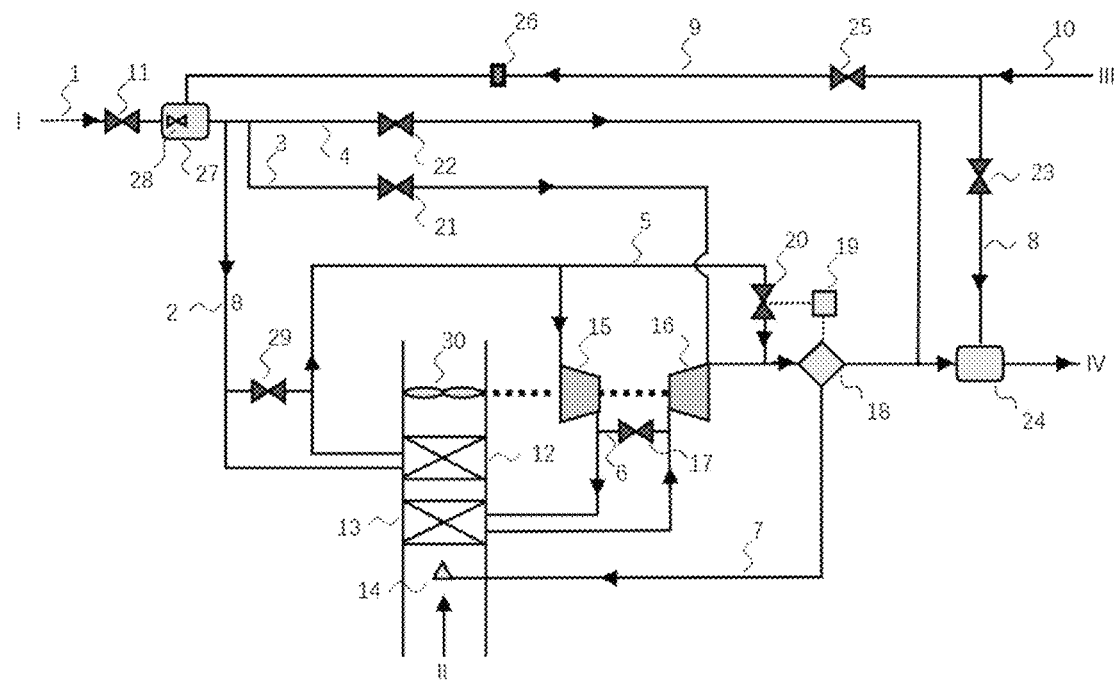
FIG. 1 shows an aircraft UHTS-ACS of the present invention.

Names for reference numerals: I, engine bleed air; II, ram air; III, recirculated air; IV, cabin supply air; 1, an engine bleed air main line (pipeline); 2, an air conditioning system main line; 3, a turbine outlet deicing bypass; 4, a supply air temperature regulating bypass; 5, a turbine outlet temperature regulating bypass; 6, a compressor superheat regulating bypass; 7, a water separation (water removal) branch; 8, an ordinary recirculated airline; 9, a ultra-high-temperature sterilization recirculated airline; 10, a recirculated air main line; 11, an engine bleed air one-way valve; 12, a primary heat exchanger; 13, a secondary heat exchanger; 14, a water sprinkler; 15, a compressor; 16, a turbine; 17, a compressor superheat regulating valve; 18, a water separator; 19, a temperature sensing and regulating device; 20, a temperature regulating valve; 21, a turbine outlet deicing valve; 22, a supply air temperature regulating valve; 23, an ordinary recirculated airline valve; 24, a mixing chamber; 25, a ultra-high-temperature sterilization recirculated airline valve; 26, a heater; 27, a high-temperature injection mixing chamber; 28, an injector; 29, a primary heat exchanger bypass valve; and 30, a fan.

Figure 2:
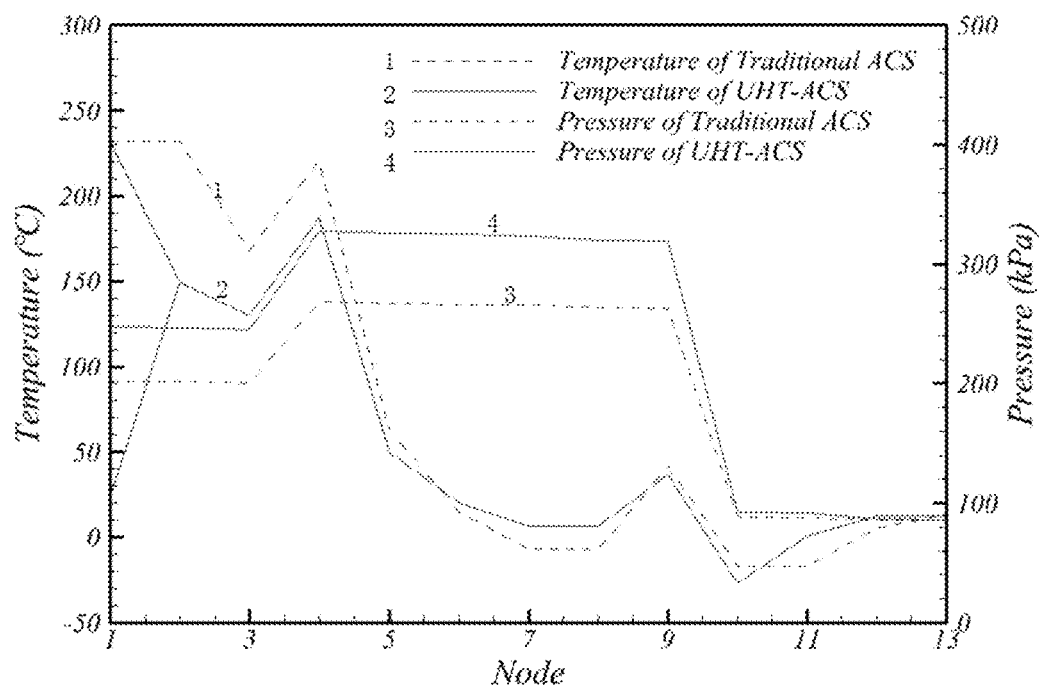

FIG. 2 is a comparison diagram of pressure and temperature distribution curves of different systems in hot weather at an altitude of 9.45 km.

Figure 3:
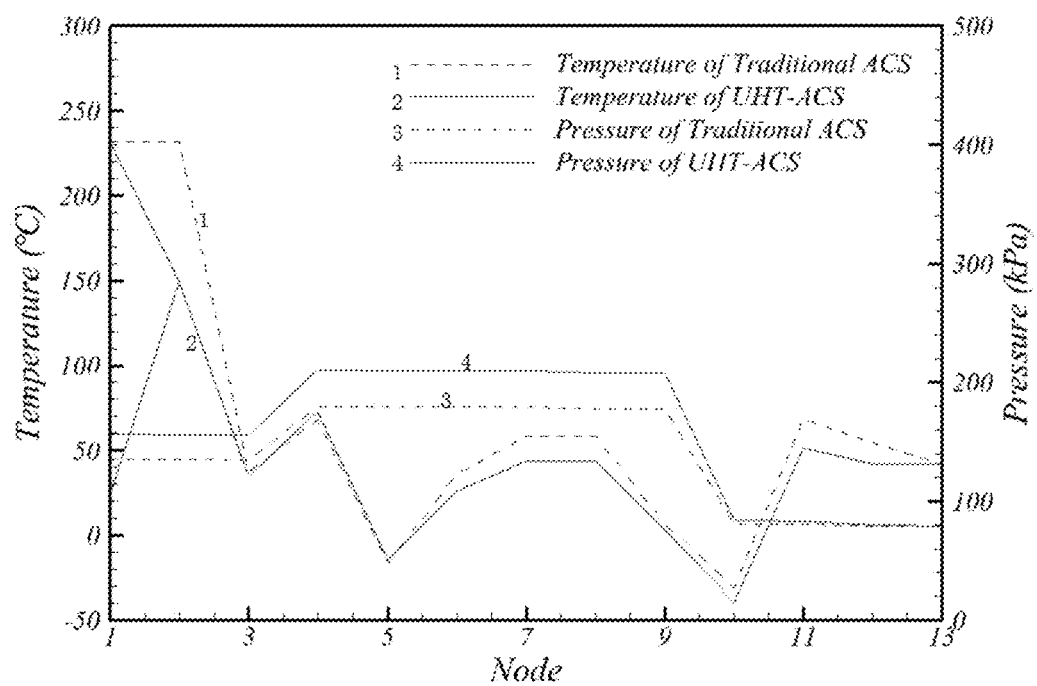

FIG. 3 is a comparison diagram of pressure and temperature distribution curves of different systems in cold weather at an altitude of 9.45 km.

DETAILED DESCRIPTION OF THE INVENTION

The solution of the aircraft UHTS-ACS of the present invention will be further described in detail below in conjunction with the accompanying drawings.

Embodiment 1

The traditional air conditioning system (traditional ACS) in aircraft (that is, the traditional system in Table 1) includes the following parts:

The air source mainly includes: 1, engine bleed air I; 2, ram air II; and 3, recirculated air III. The engine bleed air I has three lines: an air conditioning system main line 2, a turbine outlet deicing bypass 3, and a supply air temperature regulating bypass 4. High-temperature gas from the engine passes through the air conditioning system main line 2, and is subjected to heat exchange sequentially through a primary heat exchanger 12, a compressor 15, a secondary heat exchanger 13 and a turbine 16. After free water is separated by a water separator 18, the gas finally comes to a mixing chamber 24, is mixed with the recirculated air III from an ordinary recirculated air line 8, and is finally supplied to an aircraft cabin.

When the turbine outlet temperature is too low and icing occurs, a deicing valve 21 on the turbine outlet deicing bypass 3 is opened, and the high-temperature gas is led to the turbine outlet to deice the turbine.

The supply air temperature regulating bypass 4 is mainly configured to regulate the temperature supplied to the aircraft cabin to meet the design temperature requirement. The whole system includes air circulation and temperature regulation functions.

The ram air II is configured to cool the primary heat exchanger 12 and the secondary heat exchanger 13.

A water separation (water removal) branch 7 is connected to the water separator 18. The water separation (water removal) branch 7 brings the separated free water into a ram air II passage to further cool the primary heat exchanger 12 and the secondary heat exchanger 13.

According to the existing aircraft air conditioning system, after the recirculated air III is mixed with fresh air in the mixing chamber 24, the mixed gas is directly supplied to the aircraft cabin. If the recirculated air contains viruses, bacteria and the like, they cannot be effectively killed and inactivated, which is not beneficial to health and safety of people on board.

According to the aircraft UHTS-ACS of the present invention, a ultra-high-temperature sterilization recirculated air device is added on the basis of the traditional aircraft air conditioning system. The ultra-high-temperature sterilization recirculated air device includes a ultra-high-temperature sterilization recirculated airline, a high-temperature injection mixing chamber, an injector and a primary heat exchanger bypass. The ultra-high-temperature sterilization recirculated airline is connected to a recirculated air main line in the traditional aircraft air conditioning system, and the ultra-high-temperature sterilization recirculated airline is connected to the high-temperature injection mixing chamber. After recirculated air is mixed with high-temperature engine bleed air under the injection action of the injector, the mixed high-temperature gas enters a compressor through the primary heat exchanger bypass to be compressed and heated, is regulated to a suitable temperature through cooling of the secondary heat exchanger and the turbine, and then is supplied to the aircraft cabin.

Further, the primary heat exchanger bypass includes a primary heat exchanger bypass valve. The ultra-high-temperature sterilization recirculated airline is provided with a one-way valve for controlling opening and closing of the branch and a heater.

As shown in FIG. 1, the aircraft UHTS-ACS provided by the present invention mainly includes engine bleed air I, ram air II, recirculation air III, and cabin supply air IV; an engine bleed air main line (pipeline) 1, an air conditioning system main line 2, a turbine outlet deicing bypass 3, a supply air temperature regulating bypass 4, a turbine outlet temperature regulating bypass 5, a compressor superheat regulating bypass 6, a water separation (water removal) branch 7, an ordinary recirculated airline 8, the ultra-high-temperature sterilization recirculated airline 9, and a recirculated air main line 10; and an engine bleed air one-way valve 11, a primary heat exchanger 12, the secondary heat exchanger 13, a water sprinkler 14, the compressor 15, the turbine 16, a compressor superheat regulating valve 17, a water separator 18, a temperature sensing and regulating device 19, a temperature regulating valve 20, a turbine outlet deicing valve 21, a supply air temperature regulating valve 22, an ordinary recirculated airline valve 23, a mixing chamber 24, a ultra-high-temperature sterilization recirculated airline valve 25, the heater 26, the high-temperature injection mixing chamber 27, the injector 28, the primary heat exchanger bypass valve 29, and a fan 30.

TABLE 1

Comparison of temperature between traditional ACS and UHTS-ACS under different working conditions

| Temperature (° C.) | Hot weather at an altitude of 9.45 km | | Cold weather at an altitude of 9.45 km | |
| --- | --- | --- | --- | --- |
| | Traditional ACS | UHTS-ACS | Traditional ACS | UHTS-ACS |
| Engine bleed air | 232.0 | 232.0 | 232.0 | 232.0 |
| High-temperature mixing chamber | 232.0 | 148.8 | 232.0 | 148.8 |
| Compressor inlet | 167.9 | 129.7 | 37.0 | 34.8 |
| Compressor outlet | 219.9 | 186.8 | 68.0 | 72.7 |
| Secondary heat exchanger outlet | 62.4 | 49.8 | −16.2 | −14.8 |
| Condenser inlet | 14.7 | 19.8 | 36.2 | 26.1 |
| Turbine inlet | 41.6 | 36.7 | 6.3 | 2.9 |
| Turbine outlet | −16.9 | 0.4 | 68.2 | 51.2 |
| Supply air mixing chamber | 12.4 | 12.1 | 42.0 | 42.0 |

As shown in FIG. 2, FIG. 3 and Table 1, the aircraft traditional ACS and the UHTS-ACS of the present invention under different working conditions are subjected to numerical simulation analysis, and the system pressure and temperature distributions are as shown in the figures. It can be found through comparative analysis that the aircraft UHTS-ACS of the present invention can meet the requirements of aircraft cabin's cooling and heating, and the temperature of the turbine outlet is increased to some extent as compared with the traditional ACS, which is more beneficial to anti-icing and deicing of the turbine outlet.

Embodiment 2

Based on the above embodiment, in order to further enhance the sterilization effect, the heater is connected to a main line of the ultra-high-temperature sterilization recirculated air line, and the recirculated air is heated by the heater, and then rapidly mixed with the engine bleed air in the ultra-high-temperature injection mixing chamber under the injection action of the injector.

During epidemics of some novel infectious viruses or bacteria, the ordinary recirculated airline valve is closed, the ultra-high-temperature sterilization recirculated airline valve is opened, and the primary heat exchanger bypass valve is opened. At this time, the ultra-high-temperature sterilization recirculated airline works, and the ordinary recirculated airline does not work. The recirculated air is heated by the heater for preliminary sterilization. Then, the recirculated air is thoroughly mixed with the engine bleed air from the engine bleed air main line in the high-temperature injection mixing chamber under the action of the injector, so that the mixed gas can be sterilized under the action of high temperature. The mixed gas enters the compressor through the primary heat exchanger bypass to be compressed by the compressor such that the temperature of the mixed gas further increases, thereby further performing sterilization. Finally, the mixed gas is subjected to the heat dissipation of the secondary heat exchanger and the cooling of the turbine, and is subjected to temperature regulation to reach a suitable temperature through the turbine outlet deicing bypass, the turbine outlet temperature regulating bypass, the compressor superheat regulating bypass 6 and the supply air temperature regulating bypass 4, and then is supplied to the cabin. The free water is discharged out of the system through the water separation (water removal) branch.

Based on the above aircraft UHTS-ACS, the specific operation and implementation method of the system of the present invention is as follows:

1. Under special working conditions (for example, during epidemics of some novel infectious viruses or bacteria), the ordinary recirculated airline valve 23 is closed, and the ultra-high-temperature sterilization recirculated airline valve 25 is opened. The ultra-high-temperature sterilization recirculated airline 9 works, the ordinary recirculated airline 8 does not work, and the recirculated air III enters the ultra-high-temperature sterilization recirculated airline 9 through the ultra-high-temperature sterilization recirculated airline valve 25.

2. The recirculated air enters the ultra-high-temperature sterilization recirculated airline 9 and then is heated by the heater 26, so that the temperature increases and preliminary sterilization is performed on harmful bacteria and viruses in the gas.

3. The recirculated air in the ultra-high-temperature sterilization recirculated airline 9 rapidly enters the high-temperature injection mixing chamber 27 under the injection action of the injector 28, and is thoroughly mixed with the high-temperature engine bleed air I, so that the mixed gas has higher temperature, thereby further achieving the effect of sterilization. Due to the action of the injector 28, the gas is mixed more thoroughly in the high-temperature mixing chamber, and the temperature is more uniform, so that the sterilization effect is better.

4. At this time, the primary heat exchanger bypass valve 29 is opened, and the mixed gas passes through the primary heat exchanger bypass to avoid heat exchange and cooling of the primary heat exchanger 12, so that the continuous ultra-high-temperature sterilization of the mixed gas can be ensured.

5. Then the mixed gas enters the compressor 15 to be compressed by the compressor 15 such that the temperature of the mixed gas further increases, thereby further performing sterilization.

6. Finally, the mixed gas is regulated to a suitable temperature through the heat dissipation of the secondary heat exchanger 13 and the cooling of the turbine 16, and then becomes aircraft cabin supply air IV.

In the present invention, by using the aircraft engine bleed air and compressor-turbine mechanism, ultra-high-temperature sterilization are performed on the infectious viruses and bacteria in the recirculated air of the aircraft cabin under certain high temperature and pressure conditions by means of front-end mixing, thereby enhancing the air quality of the aircraft cabin supply air, inhibiting the transmissibility of aircraft cabin viruses, and ensuring the health and safety of aircraft passengers and crew on board.

The above is only the preferred embodiment of the invention. It should be pointed out that for ordinary technicians in the technical field, some improvements can be made without departing from the principle of the invention, and these improvements should also be regarded as the protection scope of the invention.

The invention claimed is:

1. An aircraft Ultra-High-Temperature Sterilization Air Conditioning System (UHTS-ACS), wherein an ultra-high-temperature sterilization recirculated air device is added on the basis of a traditional aircraft air conditioning system, and the ultra-high-temperature sterilization recirculated air device comprises an ultra-high-temperature sterilization recirculated air duct,
a heater,
a high-temperature injection mixing chamber, and
a primary heat exchanger bypass;
wherein
the ultra-high-temperature sterilization recirculated air duct is connected to a recirculated air main line in the traditional aircraft air conditioning system;
the ultra-high-temperature sterilization recirculated air duct is connected to the high-temperature injection mixing chamber,
so that ultra-high-temperature sterilization recirculated air, after being preheated by the heater, is then mixed with high-temperature engine bleed air in the high-temperature injection mixing chamber, and
the mixed high-temperature gas enters a compressor through the primary heat exchanger bypass to be compressed and heated, is subsequently cooled by a secondary heat exchanger and a turbine to a suitable temperature, and then is supplied to an aircraft cabin.

2. The aircraft UHTS-ACS according to claim 1, wherein the primary heat exchanger bypass is provided with a primary heat exchanger bypass valve for controlling opening and closing of a branch.

3. The aircraft UHTS-ACS according to claim 1, where in the ultra-high-temperature sterilization recirculated air duct is provided with a one-way valve for controlling opening and closing of a branch and the heater.

4. The aircraft UHTS-ACS according to claim 1, wherein an injector for rapid gas mixing is arranged in the high-temperature injection mixing chamber such that the temperature of the mixed high-temperature gas is more uniform.

5. The aircraft UHTS-ACS according to claim 4, wherein the heater is connected to a main line of the ultra-high-temperature sterilization recirculated air duct, and the recirculated air is heated by the heater, and then rapidly mixed with the high-temperature engine bleed air in the high-temperature injection mixing chamber under the injection action of the injector.

6. A sterilization method based on the aircraft Ultra-High-Temperature Sterilization Air Conditioning System (UHTS-ACS) according to claim 5, wherein the sterilization method comprises the following steps:

step one, closing an ordinary recirculated air duct valve, opening an ultra-high-temperature sterilization recirculated air duct valve and opening a primary heat exchanger bypass valve; heating recirculated air by the heater to increase the temperature;

step two, rapidly mixing the recirculated air with high-temperature engine bleed air in the high-temperature injection mixing chamber under the injection action of an injector in the high-temperature injection mixing chamber such that the temperature of the recirculated air rapidly increases and ultra-high-temperature sterilization is further performed;

step three, making mixed air directly enter the compressor through the primary heat exchanger bypass to be compressed and heated by the compressor such that the temperature of the mixed gas increases again, thereby sterilizing the mixed gas; and step four, after the mixed gas is cooled by the secondary heat exchanger and the turbine and subjected to temperature regulation to reach a suitable temperature, supplying the mixed gas to an aircraft cabin;

wherein the injector for rapid gas mixing is arranged in the high-temperature injection mixing chamber such that the temperature of the mixed gas is more uniform;

wherein the heater is connected to the main line of the ultra-high-temperature sterilization recirculated air duct, and the recirculated air is heated by the heater, and then rapidly mixed with the high-temperature engine bleed air in the high-temperature injection mixing chamber under the injection action of the injector.

\* \* \* \* \*